US010013260B2

(12) United States Patent
Trethewey

(10) Patent No.: US 10,013,260 B2
(45) Date of Patent: Jul. 3, 2018

(54) CONTROLS AND INDICATORS WITH ON-SCREEN COGNITIVE AIDS

(71) Applicant: Intel Corporation, Santa Clara, CA (US)

(72) Inventor: Jim R. Trethewey, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 1013 days.

(21) Appl. No.: 14/261,002

(22) Filed: Apr. 24, 2014

(65) Prior Publication Data

US 2014/0304004 A1    Oct. 9, 2014

Related U.S. Application Data

(62) Division of application No. 11/545,588, filed on Oct. 11, 2006, now Pat. No. 8,739,035.

(51) Int. Cl.
*G06F 9/44* (2018.01)
*G06F 3/048* (2013.01)
(Continued)

(52) U.S. Cl.
CPC .......... *G06F 9/4411* (2013.01); *G06F 1/1626* (2013.01); *G06F 1/1632* (2013.01);
(Continued)

(58) Field of Classification Search
None
See application file for complete search history.

(56) References Cited

U.S. PATENT DOCUMENTS 7,228,329 B2   6/2007  Kaiser
2003/0184782 A1*  10/2003  Perkins .................. G06F 3/1204
                                                     358/1.13
(Continued)

OTHER PUBLICATIONS

Gerry Kennedy, Intellikeys: Product Information, IntelliKeys Product Information, Jul. 2000, pp. 1-2.
(Continued)

*Primary Examiner* — Qing Yuan Wu
(74) *Attorney, Agent, or Firm* — Schwegman Lundberg & Woessner, P.A.

(57) ABSTRACT

The invention relates to an applet for a mobile computing device, comprising an element to detect user input and perform appropriate associated actions, and to provide a cognitive aid for users of the mobile computing device. The invention also relates to a method for controlling operation of a mobile computing device, comprising detecting user input and performing appropriate associated actions and providing a cognitive aid for users of the mobile computing device. The invention further relates to a cognitive aid for a mobile computing device having a display screen, the cognitive aid being displayed on the display screen and including an on-screen and/or an audio tip, and being associated with an input vehicle of the mobile computing device. The cognitive aid provides relevant information to the user regarding the input vehicle. The invention still further relates to a method for assisting users of a mobile computing device having a display screen. The method comprises providing a vehicle for user input to the mobile computing device and providing a cognitive aid on the display screen, the cognitive aid being associated with the user input vehicle. The cognitive aid provides relevant information to the user regarding the user input vehicle.

8 Claims, 14 Drawing Sheets

(51) Int. Cl.
*G06F 3/038* (2013.01)
*G06F 9/445* (2018.01)
*G06F 13/10* (2006.01)
*G06F 9/4401* (2018.01)
*G06F 1/16* (2006.01)
*G06F 1/20* (2006.01)
*G06F 19/00* (2018.01)
*G06F 3/0484* (2013.01)
*G16H 40/63* (2018.01)
*G16H 10/60* (2018.01)
*G06F 9/451* (2018.01)

(52) U.S. Cl.
CPC .......... *G06F 1/1656* (2013.01); *G06F 1/1684* (2013.01); *G06F 1/1686* (2013.01); *G06F 1/1698* (2013.01); *G06F 1/203* (2013.01); *G06F 3/038* (2013.01); *G06F 3/048* (2013.01); *G06F 3/0484* (2013.01); *G06F 9/44505* (2013.01); *G06F 9/453* (2018.02); *G06F 13/102* (2013.01); *G06F 19/3418* (2013.01); *G16H 10/60* (2018.01); *G16H 40/63* (2018.01); *G06F 2200/1632* (2013.01)

(56) References Cited

U.S. PATENT DOCUMENTS

2004/0212610 A1* 10/2004 Hamlin ................ G06F 3/1423
                                                            345/211
2007/0282208 A1    12/2007 Jacobs et al.

OTHER PUBLICATIONS

"U.S. Appl. No. 11/545,588, Advisory Action dated Sep. 27, 2012", 3 pgs.
"U.S. Appl. No. 11/545,588, Advisory Action dated Nov. 28, 2011", 2 pgs.
"U.S. Appl. No. 11/545,588, Appeal Decision dated Oct. 26, 2012", 2 pgs.
"U.S. Appl. No. 11/545,588, Final Office Action dated Jul. 6, 2012", 14 pgs.
"U.S. Appl. No. 11/545,588, Final Office Action dated Jul. 22, 2011", 13 pgs.
"U.S. Appl. No. 11/545,588, Non Final Office Action dated Feb. 14, 2013", 16 pgs.
"U.S. Appl. No. 11/545,588, Non Final Office Action dated Aug. 15, 2013", 13 pgs.
"U.S. Appl. No. 11/545,588, Non Final Office Action dated Nov. 29, 2010", 9 pgs.
"U.S. Appl. No. 11/545,588, Non Final Office Action dated Dec. 27, 2011", 13 pgs.
"U.S. Appl. No. 11/545,588, Notice of Allowance dated Jan. 15, 2014", 8 pgs.
"U.S. Appl. No. 11/545,588, Pre-Appeal Brief Request filed Oct. 9, 2012", 5 pgs.
"U.S. Appl. No. 11/545,588, Requirement Restriction dated Aug. 5, 2010", 6 pgs.
"U.S. Appl. No. 11/545,588, Response filed Mar. 27, 2012 to Non Final Office Action dated Dec. 27, 2011", 13 pgs.
"U.S. Appl. No. 11/545,588, Response filed Apr. 29, 2011 to Non Final Office Action dated Nov. 29, 2010", 13 pgs.
"U.S. Appl. No. 11/545,588, Response filed May 14, 2013 to Non Final Office Action dated Feb. 14, 2013", 10 pgs.
"U.S. Appl. No. 11/545,588, Response filed Sep. 6, 2012 to Final Office Action dated Jul. 6, 2012", 12 pgs.
"U.S. Appl. No. 11/545,588, Response filed Sep. 7, 2010 to Requirement Restriction dated Aug. 5, 2010", 1 pg.
"U.S. Appl. No. 11/545,588, Response filed Oct. 24, 2011 to Final Office Action dated Jul. 22, 2011", 12 pgs.
"U.S. Appl. No. 11/545,588, Response filed Nov. 15, 2013 to Non Final Office Action dated Aug. 15, 2013", 10 pgs.
Gerry, Kennedy, "Intellikeys: Product Information", (Jul. 2000), 1-2.

* cited by examiner

CONTROLS AND INDICATORS WITH ON-SCREEN COGNITIVE AIDS

FIELD OF INVENTION

The embodiments of the invention relate to a mobile computing device with integrated peripheral that may be used, for example, in a clinical or hospital environment for monitoring the welfare of a patient. Illustrative of mobile computing devices according to the present invention are tablet-style personal computers designed to communicate wirelessly with one or more peripherals while being convenient to hold and operate and resistant to penetration by fluids. The present invention more particularly relates to controls and indicators with on-screen cognitive aids for use with a mobile computing device.

BACKGROUND

A class of personal computers that is smaller than the typical "desktop" or "laptop" devices is known in the art as "tablet" personal computers, or tablet PCs. Such computing devices are generally known for use as personal digital assistants and as specialized, mobile computers. Tablet PC's typically offer the advantage of a small form factor that is easy for the user to carry.

The systems of known tablet PCs employ a variety of methods for mapping to buttons. Known methods for mapping to buttons in system implementations can differ from model to model and from one OEM/ODM to another. Although a small number of such features have been standardized by mapping methods such as, for example, ACPI, most are not standardized at all.

This requires that a new ACPI device driver be written every time, requiring the driver writer to coordinate with the BIOS developer to ensure that they agree on the names of the ACPI control methods and any parameters they might have.

DETAILED DESCRIPTION

Figure 1:
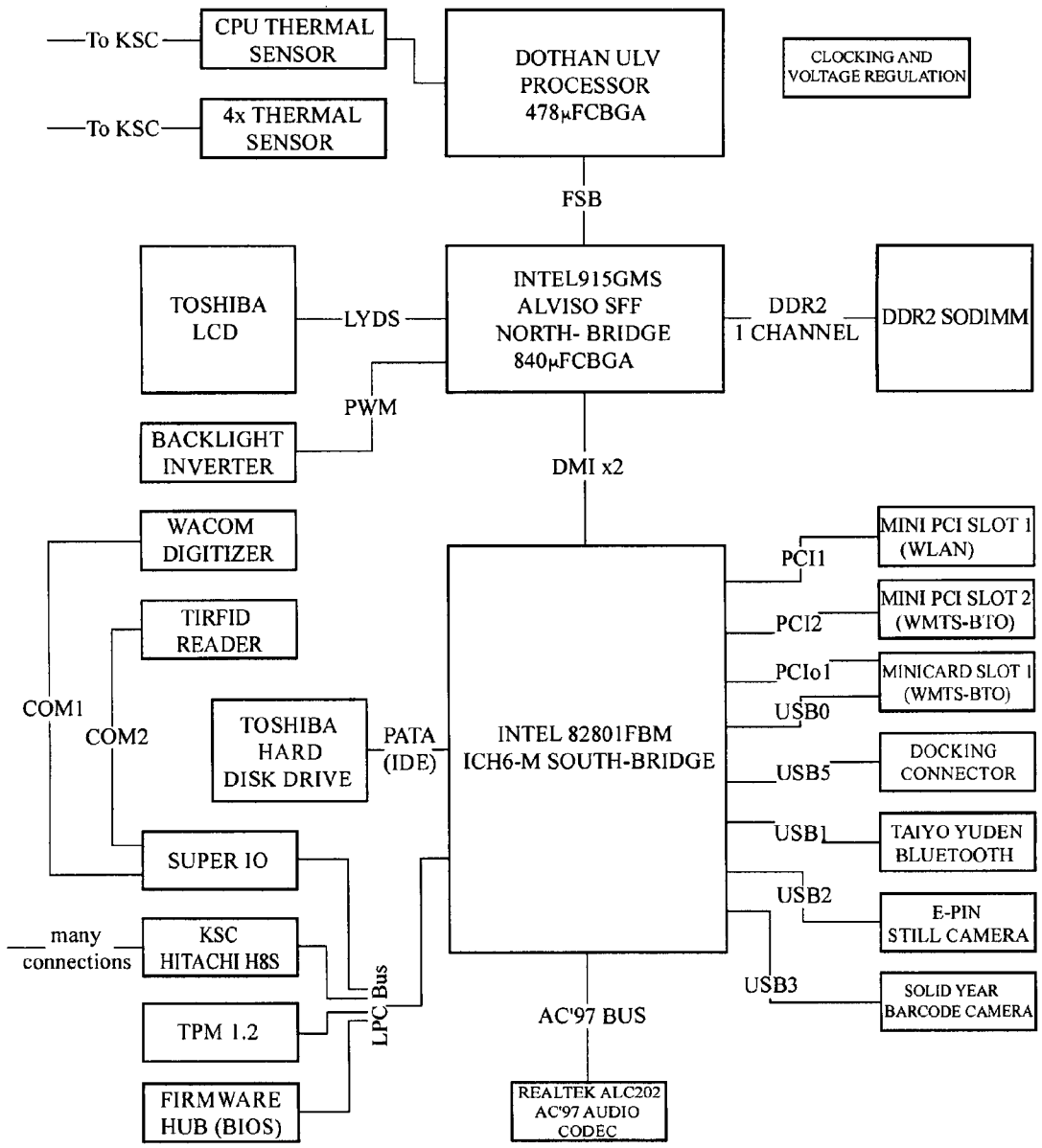
FIG. 1 is a block diagram of an illustrative embodiment of the computing hardware of the present invention.

As used in the specification and claims, the singular forms "a", "an" and "the" include plural references unless the context clearly dictates otherwise. For example, the term "an array" may include a plurality of arrays unless the context clearly dictates otherwise. Further, Table 1, below, lists various acronyms and terms of art used herein.

TABLE 1

| | |
|---|---|
| AC97 | Audio Codec 97 |
| ACPI | Advance Configuration and Power Interface |
| AHCI | Advanced Host Controller Interface (SATA) |
| ALS | Ambient Light Sensor - detects room lighting conditions |
| AOE | Intel MPG APAC ODM Enabling Operation |
| AOL | Alert On LAN |
| AON | Always On. Former name of what is now called EMA. |
| AP | Access Point |
| API | Application Programming Interface |
| ARD | Architectural Requirements Document |
| AV | Audio/Video |
| Azalia | High definition audio |
| BIA | Back Light Image Adaptation |
| BIOS | Basic Input/Output System, the PC firmware/boot ROM. |
| BLI | Back Light Inverter |
| BT | Bluetooth |
| CCU | Common Configuration Utility |
| CDS | Content Directory Service. A UPnP service that advertises media content available for sharing on a home network. |
| CE | Consumer Electronics (e.g., VCR, stereo, TV) |
| CCFL | Cold Cathode Fluorescent Light (known technology used for backlighting LCD display panels) |
| CIR | Consumer Infra Red |
| CLR | Common Language Runtime. Microsoft virtual machine for .NET languages. |
| CMT | Centrino Mobile Technology |
| COM | Serial communications port |
| CPU | Central Processing Unit |

TABLE 1-continued

| | |
|---|---|
| CRT | Cathode Ray Tube |
| DDR | Double Data Rate |
| DH | Digital Home |
| DHWG | Digital Home Working Group |
| DLL | Windows Dynamic Link Library |
| DMA | Digital Media Adaptor (Digital Home context) or Direct Memory Access (device driver context). |
| DMI | Direct Media Interface |
| DPG | Intel Desktop Products Group |
| DPST | Display Power Saving Technique |
| DRAM | Dynamic Random Access Memory |
| DSP | Digital Signal Processor (a chip) or Digital Signal Processing (as in algorithms) |
| DTCP | Digital Transmission Copy Protection |
| DTLA | Digital Transmission Licensing Authority |
| DVB | Digital Video Broadcast. A digital television transmission standards family (as opposed to analog television standards such as NTSC and PAL), used in most regions of the world other than the United States and Japan. DVB-T refers to "terrestrial" (over the air) transmission, DVB-C is cable transmission, DVB-S is satellite transmission, and DVB-H is a format tailored to handheld devices such as cell phones. |
| DVD | Digital Video Disk |
| DVI | Digital Video Interface, a successor to VGA for digital video interface to monitors and TVs. In addition to having digital video pins, the DVI connector also has provision for legacy analog VGA pins, such that a "converter dongle" may be used to adapt a DVI connector to a VGA monitor/projector. Unlike HDMI, DVI connectors can output video only. |
| EBL | Extended Battery Life |
| EC | Embedded Controller, e.g., Hitachi H8 |
| EEPROM | Electrically Erasable Programmable Read Only Memory |
| EF | East Fork - initiative to include multiple new features into a branded platform. Functions and requirements defined in this document. |
| EL | Energy Luminescent panel |
| EMA | Extended Mobile Access |
| ENU | English, as spoken in the United States |
| EPG | Electronic Program Guide (like a TV Guide, obtained and viewed electronically) |
| ESM | Spanish, as spoken in Mexico |
| ETM | Extended Thermal Model (Camarillo run-time software) |
| FCBGA | Flip Chip Ball Grid Array (known form factor used for packing silicon chips such as CPUs) |
| FIR | Fast Infra Red |
| FW | Firmware |
| FWH | Firm Ware Hub, the flash memory chip that contains the BIOS |
| GMCH | Graphics Memory Controller Hub |
| GPIO | General Purpose Input Output |
| GPRS | General Packet Radio Service, a system devised to enable data TCP/IP data communication over GSM networks. |
| GPS | Global Positioning System, developed by the U.S. military for navigation and surveying. It relies on satellites for precise determination of locations. |
| GSM | Global System for Mobile communications, the most dominant of all second-generation digital mobile telephony standards. |
| GUI | Graphical User Interface |
| HD | High Definition |
| HDA | High Definition Audio ("Azalia") |
| HDD | Hard Disk Drive |
| HDMI | High Definition Multimedia Interface, a successor to DVI for high definition monitors and TVs. It is possible to buy adaptor cables from DVI to HDMI. Unlike DVI, HDMI connectors can also output audio. |
| HIBCC | Healthcare Industry Bar Code standard (data format for asset tagging using barcode or RFID). See http://www.hibcc.org |
| HIPAA | Health Insurance Portability and Accountability Act. See http://www.hipaa.org/ |
| HW | Hardware |
| IA | Intel Architecture. IA-32 is 32-bit architecture. IA-32e is 32-bit architecture with 64-bit extensions. IA-64 is 64-bit architecture (Itanium family). |
| ICH | Input Output Controller Hub |
| ICS | Windows Internet Connection Sharing |
| IHV | Independent Hardware Vendor |
| ISV | Independent Software Vendor |
| IDE | Integrated Device Electronics |
| KSC | Keyboard/System Controller, H8 microcontroller used for keyboard scan, battery charging, and miscellaneous system GPIO's. |
| LAN | Local Area Network |

TABLE 1-continued

| | |
|---|---|
| LED | Light Emitting Diode |
| LH | Longhorn |
| LOM | LAN On Motherboard |
| LPC | Low Pin Count |
| LTO | Long Term Orbit. A type of Assisted GPS data file obtained over the Internet and optionally cached on the notebook hard drive. This data file contains predictive GPS satellite orbit tracks for 48 hours into the future. |
| LVDS | Low Voltage Differential Signaling, a style of LCD panel interface |
| MB | Mother Board |
| MCH | Memory Controller Hub |
| MCE | Media Center Edition |
| MDC | Mobile Daughter Card |
| MDH | Mobile Digital Home |
| MEF | Mobile East Fork |
| MEP | Modular Embedded Protocol, an electrical and messaging bus promulgated by Synaptics Corp. |
| MPA | Intel MPG Mobile Platform Architecture Operation |
| MPEG | Motion Picture Experts Group, standards body creating specifications for video encoding formats such as MPEG2 and MPEG4. |
| MPG | Intel Mobile Platforms Group |
| MS or MSFT | Microsoft |
| N/A | Not Applicable |
| NAT | Network Address Translation |
| N/C | Not connected. Refers to an optional feature (usually an electrical signal) which is not used on a design, and so is left unconnected. |
| NIC | Network Interface Controller |
| NMA | Network Management Application |
| NMPR | Intel Network Media Product Requirements |
| NOA | Node Observation Architecture |
| NTSC | NTSC is the analog television system in use in Korea, Japan, United States, Canada and certain other places, mostly in the Americas. It is named for the National Television System(s) Committee, the industry-wide standardization body that created it. The term "NTSC" is often used informally to refer to a 525-line/60 Hz (principally USA/Japan) television system, and to differentiate from a 625-line/50 Hz (principally European) "PAL" system. |
| ODD | Optical Disc Drive |
| ODM | Original Design Manufacturer |
| OEM | Original Equipment Manufacturer |
| OOBE | Out Of Box Experience, what the user experiences when they first unpack the product from the box and try to install/use it. |
| OS | Operating System |
| PAL | PAL, short for phase-alternating line, phase alternation by line or for phase alternation line, is a color encoding system used in broadcast television systems in large parts of the world. Other common analog television systems are SECAM and NTSC. PAL was developed by Walter Bruch at Telefunken in Germany, and the format was first introduced in 1967. The term "PAL" is often used informally to refer to a 625-line/50 Hz (principally European) television system, and to differentiate from a 525-line/60 Hz (principally USA/Japan) "NTSC" system. |
| PATA | Parallel AT Attachment, a style of HDD or ODD interface |
| PC | Personal Computer |
| PCB | Printed Circuit Board |
| PCI | Peripheral Connect Interface |
| PCIe | Peripheral Connect Interface Express |
| PDO | Intel MPG Platform Delivery Operation |
| PGA | Pin Grid Array |
| PL | Precision Location |
| PRD | Product Requirement Document |
| PSB | Processor System Bus |
| PVR | Personal Video Recorder, also known as a DVR, Digital Video Recorder |
| PWM | Pulse Width Modulation |
| RAID | Redundant Array of Inexpensive Disks |
| RAM | Random Access Memory |
| RFC | "Request For Comment", an IETF specification |
| RFID | Radio Frequency Identification |
| RIO | UPnP Remote I/O |
| ROM | Read Only Memory |
| RS-232 | An electronics industry association (EIA) standard for serial communications. |
| RSIO | Reduced Super Input Output |
| RTC | Real Time Clock |
| RX | Receive |
| SATA | Serial AT Attachment, a style of HDD or ODD interface |

TABLE 1-continued

| | |
|---|---|
| SCI | System Control Interrupt, the mechanism that en embedded controller uses to signal the host CPU in certain motherboard designs. |
| SDVO | Serial Digital Video Output |
| SIO | Super Input Output |
| SIM | Subscriber Identity Module, a miniature "smart card" inserted into GSM phones that may securely contain identification information and encryption keys, as well as in some cases, a protected encryption execution environment. |
| SMC | System Management Controller |
| SMPTE | Society of Motion Picture and Television Engineers (SMPTE) refers to this test pattern as Engineering Guideline EG 1-1990. The components of this pattern are a known standard, so comparing this pattern as received to that known standard gives video engineers an indication how an NTSC video signal has been altered by recording or transmission, and thus what compensation needs to be applied to that signal to bring it back to original condition. The pattern is also used for setting a television monitor or receiver to reproduce NTSC chrominance and luminance information correctly. |
| SOAP | Simple Object Access Protocol, an XML-based lightweight protocol for exchange of information in a decentralized, distributed environment. |
| SODIMM | Small Outline Dual In Line Memory Module |
| Soft AP | Soft Access point |
| SPDIF | Sony/Philips Digital Interface |
| SSL | Secure Sockets Layer |
| STA | Wireless LAN station (client of an AP) |
| STAT | System Thermal Analysis Tool |
| STB | Set Top Box |
| STM | Synaptics ™ Touch Module, a printed circuit board containing a plurality of buttons and indicators, manufactured by Synaptics Corp. |
| SV | System Validation |
| SW | Software |
| TBD | To Be Determined |
| TFT | Thin Film Transistor, a known technology used in the design and fabrication of pixel cells in LCD display panels. |
| TPM | Trusted Platform Module |
| TPV | Third Party Vendor |
| TV | Television |
| TX | Transmit |
| UHCI | Universal Host Controller Interface |
| UI | User Interface. Often graphical, see GUI. |
| UPnP | Universal Plug and Play |
| USB | Universal Serial Bus |
| UWB | Ultra Wide Band, former name of Wireless USB |
| VCOM | Virtual COMmunications port, a device driver that looks like a real COM port, but has no physical COM hardware associated with it. |
| VCR | Video Cassette Recorder |
| VGA | Video Graphics Array |
| VO | Visual Off (Energy Lake Lite) |
| VOIP | Voice Over Internet Protocol |
| VPN | Virtual Private Network |
| WLAN | Wireless Local Area Network |
| WMA | Microsoft Windows Media Audio |
| WMTS | Wireless Medical Telemetry Service |
| WMV | Microsoft Windows Media Video |
| WNG | Intel Wireless Networking Group |
| WOL | Wake on LAN |
| WoW | Wake on Wireless LAN |
| WoWLAN | Wake on Wireless LAN |
| WWAN | Wireless Wide Area Network |
| WZC | Windows Zero Configuration, an automatic WLAN configuration scheme. |
| WZP | Windows Zero Provisioning, a follow-on to WZC that also provides for automatic provisioning of DSL at home or WLAN at hotspots. |

In one embodiment, the invention relates to an applet for a mobile computing device, comprising an element to detect user input and perform appropriate associated actions, and to provide a cognitive aid for users of the mobile computing device. The element utilizes a single device driver to detect and perform appropriate actions associated with the user input. The device driver can be an ACPI-to-HID mapper driver. User input can be via button presses. The cognitive aid can comprise an on-screen tip and/or an audio tip. An on-screen tip can be provided for each button. A configuration file can define details of user input implementation, and the details are read by the applet.

The invention also relates to a method for controlling operation of a mobile computing device, comprising detecting user input and performing appropriate associated actions and providing a cognitive aid for users of the mobile computing device.

The invention further relates to a cognitive aid for a mobile computing device having a display screen, the cognitive aid being displayed on the display screen and being associated with an input vehicle of the mobile computing device that is connected to an embedded controller. The cognitive aid provides relevant information to the user regarding the input vehicle via on-screen tips and/or audio tips.

The invention still further relates to a method for assisting users of a mobile computing device having a display screen. The method comprises providing a vehicle for user input to the mobile computing device and providing a cognitive aid on the display screen, the cognitive aid being associated with the user input vehicle. The cognitive aid provides relevant information to the user regarding the user input vehicle.

The invention also relates to a mobile computing device having an element with standardized nomenclature for controlling HID-class buttons. The standardized nomenclature is adapted to allow a single device driver to control all types of buttons, and map them to HID class button events, and to be re-usable for a variety of mobile computing device implementations. The device driver can be an ACPI-to-HID mapper driver. A configuration file can define details of HID-class button implementation, which are used to control the ACPI-to-HID mapper driver without changing source code for the ACPI-to-HID mapper driver.

The invention further relates to an applet for a mobile computing device having a user input vehicle, comprising an element adapted to provide an end-user management graphical user interface and to gain knowledge about the user input vehicle by reading a configuration file and communicating via a device driver without changing source code for the device driver or the applet. The mobile computing device can be configured for a variety of sites having different application requirements. The user input vehicle can be configurable for a site-specific application.

An illustrative embodiment of the computer hardware component of a mobile computing device according to the present invention is shown in FIG. 1. For exemplary purposes, the below discussion of the invention is embodied in a tablet PC. As shown, the tablet PC motherboard includes a CPU. In this embodiment, the illustrative CPU is a 478-ball Dothan ULV processor in a Micro-FCBGA package. The CPU may be soldered down to the motherboard or it may be socketed to facilitate the replacement of defective units, to permit the end-user to upgrade the processor, etc. The selected CPU runs nominally at 1.2 GHz in High Frequency mode and at 600 MHz in Low Frequency mode. Other CPUs may be used, although size, heat dissipation, and power requirements may change in other parts of the system. Those skilled in the art will recognize and be able to adapt hardware aspects that must be accommodated for other processors.

Faster processors, for example, may be larger in size and generate more heat while consuming more power; and smaller processors may require less power and generate less heat that must be removed from the system. The selected CPU can also support enhanced technologies for voltage and frequency scaling.

The system memory may be determined based on the intended application of the tablet PC through the use of commercially available memory modules. The illustrative embodiment of FIG. 1 may contain a single-channel, 400 MHz DDR2 capable SODIMM socket. A default configuration employing one DRAM module of 1 GB size can accommodate a wide-variety of applications, although larger and smaller DRAM modules are available and can be installed at the time of manufacturing. In applications where the memory is not hard-wired to the motherboard and the tablet PC chassis permits opening by the user, the user or technician may be provided with the ability to change memory modules to replace defective units or increase memory capacity.

A variety of commercially-available system clocks may be employed, as well. An exemplary embodiment of the present invention may employ a CK-410M Clock Synthesizer.

In communication with the processor via the motherboard's front-side bus might be the GMCH, or "North Bridge" as it is commonly referred to in the art. The GMCH (memory and graphics controller) functions can be provided by an Alviso SFF graphics/memory controller hub model "915GMS," and packaged in an 840-ball, 27 mm×27 mm Micro-FCBGA package and is usually soldered to the motherboard. It may, in some instances, be useful to provide the GMCH in a socketed configuration, if convenient substitution of the unit is desirable.

Video capability may be provided via a TFT, LCD, or other flat-panel display that can be incorporated into the chassis of the device. In the present embodiment, only a single display is required, thus the analog TV-Out and digital SDVO outputs can be disabled on the graphics controller. Only the LVDS interface to an LCD panel, or other, is necessary. Other outputs may be enabled and external ports may be provided, with adequate safeguards taken to avoid increasing the risk of fluid incursion into the chassis, in instances where external video is desirable.

The ICH, also referred to as the "South Bridge", provides I/O capabilities. In one embodiment of the present tablet, these services are provided by the ICH6-M I/O controller hub (ICH). This ICH may provide an x2 DMI interface to the "North Bridge", a PCI Bus which can be routed to one or more MiniPCI card connectors, a PCI Express (PCIe) Bus which may be routed to one or more MiniCard card connectors, a PATA interface for providing a data path to a hard disk drive, and a SATA interface. The SATA interface may or may not be used, depending on the number and types of data storage units required. Other storage device interfaces may be used, as well, if a different ICH is selected for use in the tablet.

The ICH can also provide USB ports. The ICH6-M ICH provides Eight (8) USB ports for devices such as cameras, barcode readers, Bluetooth wireless communications controllers, docking connectors, etc. Other ICHs may provide more or less, depending on the needs of the system and the anticipated number of USB peripherals. As well, the ICH should provide an audio bus, to provide the device with sound capability. The ICH of this illustrative embodiment is; configurable for AC97 or Azalia High-Definition Audio.

The ICH can also provide a LPC (Low Pin Count) Bus. The LPC bus may connect to the firmware hub, i.e., the Flash EEPROM storing the BIOS code and support the use of a KSC or embedded controller (in this embodiment a Hitachi H-8 Keyboard/System Controller). The LPC may also provide a communications path to a Super-I/O chip with two RS-232C serial ports; and a TPM (Trusted Platform Module) chip that provides security key storage. Variations between available ICHs may permit different hardware to be connected to the system via the ICH to accommodate varying hardware configurations.

The system may also employ thermal sensors to permit monitoring of thermal conditions within the chassis and for various components on the motherboard. Most modern CPU's, such as the one employed in the exemplary embodiment, include an on-die thermal sensor. Further, an external thermal diode positioned very near the CPU package can be connected to a remote thermal sensor. The remote thermal sensor's SMBus may interface with the KSC's SMBus and also with the processor's "Critical Thermal" pin. When the "Critical Thermal" pin is driven, the processor is designed to perform an emergency shutdown. Typically, when such a shutdown occurs, the operating system state will not be saved. Prior to that event, the current temperature can be read via the KSC, and the KSC may also be programmed to provide a warning interrupt when a temperature threshold (also called a "thermal trip point") is crossed. Additional sensors may be employed to increase the level of monitoring or for system-design debugging purposes.

System power may be provided by an internal system battery pack or by mounting in a dock which provides an external connection to an AC/DC converter "brick". The battery pack can be charged through an on-board charger using, for example, a battery charger controller controlled by the KSC. The charger may then be used to charge and control the batteries and provide system regulation of +12.6 VDC when external power is provided. When only battery power is available the voltage may typically range from a maximum of about +12.6 VDC (fully charged) down to a minimum of about +9.0 VDC (at discharge cut-off). Different power supply schemes, of course, may result in variations of the minimum and maximum voltages.

The power from the two paths described above is typically input to most of the on-board voltage regulator circuits to provide power to all system components. The input voltage may be converted by various commercially available components to provide a variety of rail voltages. In the present embodiment, a 4-in-1 controller (e.g., a TPS5130) may be employed to develop the system voltage rails including, at least, +5.0V, +3.3V, +2.5V, and "+1.5V ALWAYS". Other voltage rails may be developed and supplied to peripherals and system hardware by employing appropriate voltage controllers.

Typically, chipset and memory subsystems require separate regulation to provide +1.8V, +0.9V, and +1.05V. This power may be provided by two dual regulator circuits with one providing the memory supply and the other the VCCP and GMCH core power.

Various "always" power rails may be switched using FETs (Field Effect Transistors) to provide switched rails when system S-states require power to be controlled on or off at various times.

According to the present, illustrative embodiment, six (6) Lithium prismatic cells, such as the Panasonic CGA103450A, are bundled into a single battery pack in a 3S2P geometry. A charging controller board may also be included in this package. Each cell typically provides 1950 mAh of storage nominally at 3.7 VDC, for a total pack capacity of 3900 mAh at 11.1 VDC.

At an average and continuous system consumption rate, for example about 12 W, a battery life of approximately 3½ hours on a single charge may be anticipated. When the system is in suspend or hibernate modes, battery life will be extended. During times of heavy use (complex computation), battery life will shorten.

The dock may also contain a charging cavity for a second battery, which can preferably be "warm swapped" (exchanged without powering down the system) with a discharged battery while the tablet PC is stationed in the dock and receiving A/C power.

An A/C power "brick" typically provides electrical service to the dock. The A/C power brick may be one such as the Powertron Electronics Corporation model F10653-A. This pack is designed to connect to the wall source power on one end, and the docking cradle on the other end. Such a brick may accept input at 110 VAC to 240 VAC from 47 Hz to 63 Hz, so should be usable worldwide, assuming the correct physical adaptor plug is used. Typically, units manufactured for the North American market might be supplied with a 3-prong (grounded) plug. Other plugs, of course, can be used to accommodate power outlet configurations used elsewhere in the world.

Illustratively, the power brick may provide output at +19 VDC+/−5% at a maximum of about 3.42 A and have a barrel-type plug with positive voltage on "tip" and ground on "ring". Other styles of power bricks to provide for other voltage requirements, lower voltage tolerances, and higher or lower anticipated current requirements are known in the art.

Figure 2:
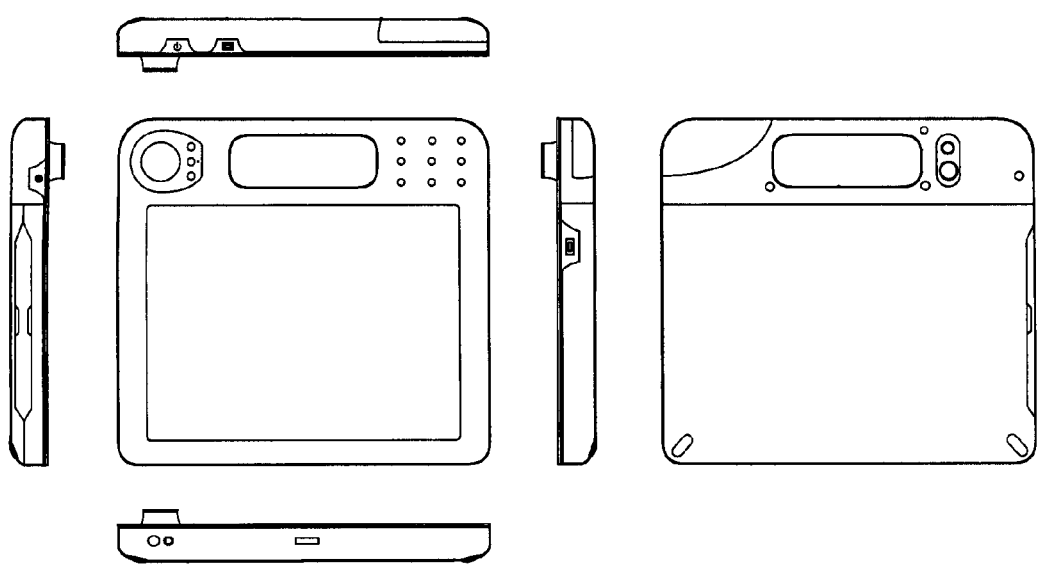
FIG. 2 is a plan view of an illustrative embodiment of the chassis of the present invention.

An embodiment of the tablet PC is illustrated in FIG. 2. As shown, the tablet PC may have a thin and light design targeted to the healthcare vertical market segment and tailored to predicted usage models primarily by nurses and secondarily by doctors. Key system design features might include a rugged, rounded, professional appearance and a sealed chassis resistant to bio-fluids and germ growth. The chassis should be constructed in a manner permitting it to withstand cleaning using anti-bacterial reagents. It is also desirable to provide an ergonomic layout with carry handle and peripheral positioning.

When used to provide a tablet-style PC for use in hospitals or a clinical environment, the chassis may be designed to provide for the integration of technological features such as a stethoscope, vital signs monitoring equiment (temperature, blood pressure, etc.), or other peripherals desired for medical professionals. In one embodiment, these devices communicate wirelessly with the tablet PC via Bluetooth, 802.11 wireless protocol, or other wireless data transmission protocol.

Figure 3:
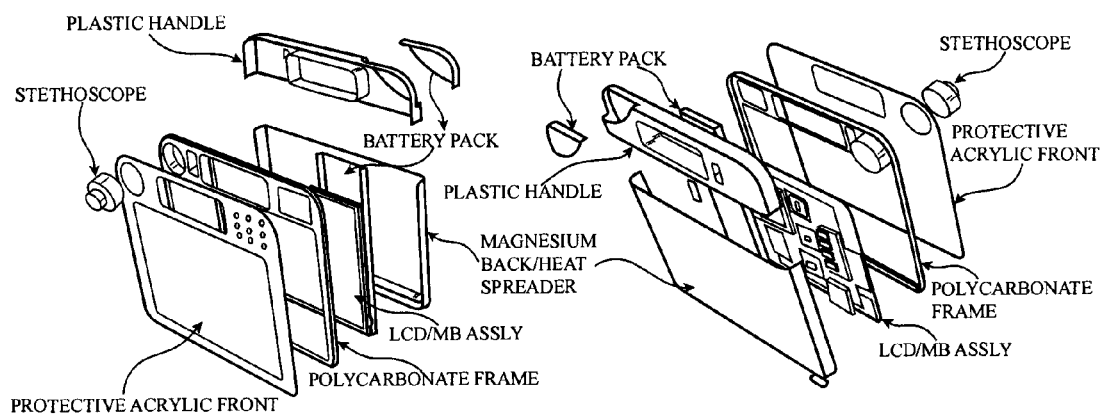
FIG. 3 is an exploded view of an embodiment of the chassis of the present invention.
Figure 4:
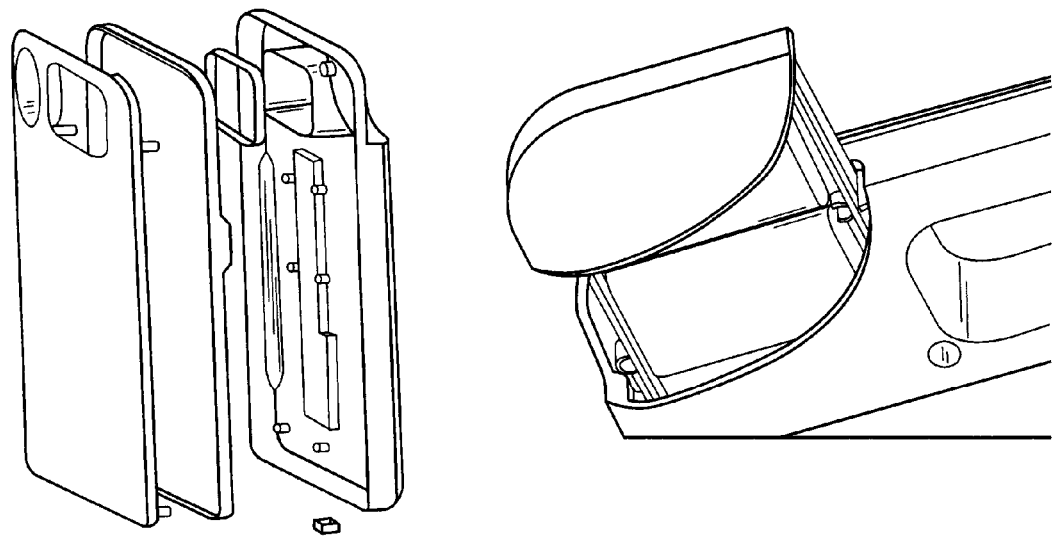
FIG. 4 is an exploded view of an embodiment of the chassis of the present invention showing an exemplary gasket structure.

The chassis may comprise the following components, illustrated in FIGS. 3 and 4: a front plate; frame, an electronic assembly for the LCD or other display screen, a digitizer (not shown), a motherboard (LCD/MB assembly) and daughter-cards (not shown). A back plate may include a handle assembly and a heat spreader/sink. It may be desirable to provide a back plate that includes a flat-plate comprised of a metal that dissipates heat quickly, such as magnesium, titanium, aluminum, copper, etc. The heat spreader plate may, as well, be in physical contact with motherboard components that require heat dissipation, such as the CPU, although such contact may be made via substances such as thermal grease or intermediate layers of heat-conductive metal. This permits the back-plate of the tablet PC to act as a heat-sink, thereby avoiding the need for internal fans or other means for heat removal that may compromise the unit's ability to resist penetration by fluids, moisture, and other contaminants.

In the illustrative embodiment, the battery pack may incorporate a cap that provides a mating seal to the handle assembly. A stethoscope, or other peripheral, may be formed to insert into a void (or recessed cavity) in the acrylic surface and rest in a cavity sculpted or otherwise formed in the frame. The construction materials, of course, are merely presented for purposes of illustration, those skilled in the art will recognize that a wide variety of metals and plastics may be substituted for any of the chassis components, provided that issues with magnetic and electrical shielding for the components and various antennae are accounted for.

To provide a chassis that is well-sealed to be water/fluid resistant and resistant to cleaning with industrial chemical solvents, or other materials, the chassis components may be assembled with interposing rubber o-ring gaskets, or similar gaskets able to provide fluid-resistance for each of the seams where chassis components meet.

All seams in a system designed to be fluid resistant should generally be gasketed to prevent fluid penetration into the system. A main gasket that seals the top and bottom subassemblies would typically be provided. This gasket also integrates the "hard" buttons (e.g., power, camera shutter, barcode/RFID scanner, etc.) to provide sealed button actuation, where buttons or a button pad are employed.

In an embodiment of the invention, the battery cap contains a rubber diaphragm that forms a compression seal against the handle area. The fasteners preferably use o-rings or silicon for sealed assembly.

In order to achieve a high degree of thermal performance, the primary components may be cooled by the integrated chassis/heatsink. For example, the chassis may be made of injection molded magnesium frame, or other suitable highly heat conductive material. The frame may then be coupled directly to the CPU, GMCH, and ICH or indirectly via thermal grease or intermediate layers of heat conductive material.

A thermal shield may be implemented over the top of the chassis/heatsink to limit the heat transfer rate from the heatsink to the user. In a preferred embodiment of the invention, no fans or system vents are provided, which maintains sealability of the system.

According to the structure describe above, the system is passively cooled. Heat is transferred out of the system via conduction, natural convection, and radiation. An insulating shield may be applied to the back of the display screen, for example an LCD, to maintain its required ambient temperature and provide a more uniform temperature profile across the surface of the display.

Figure 5:
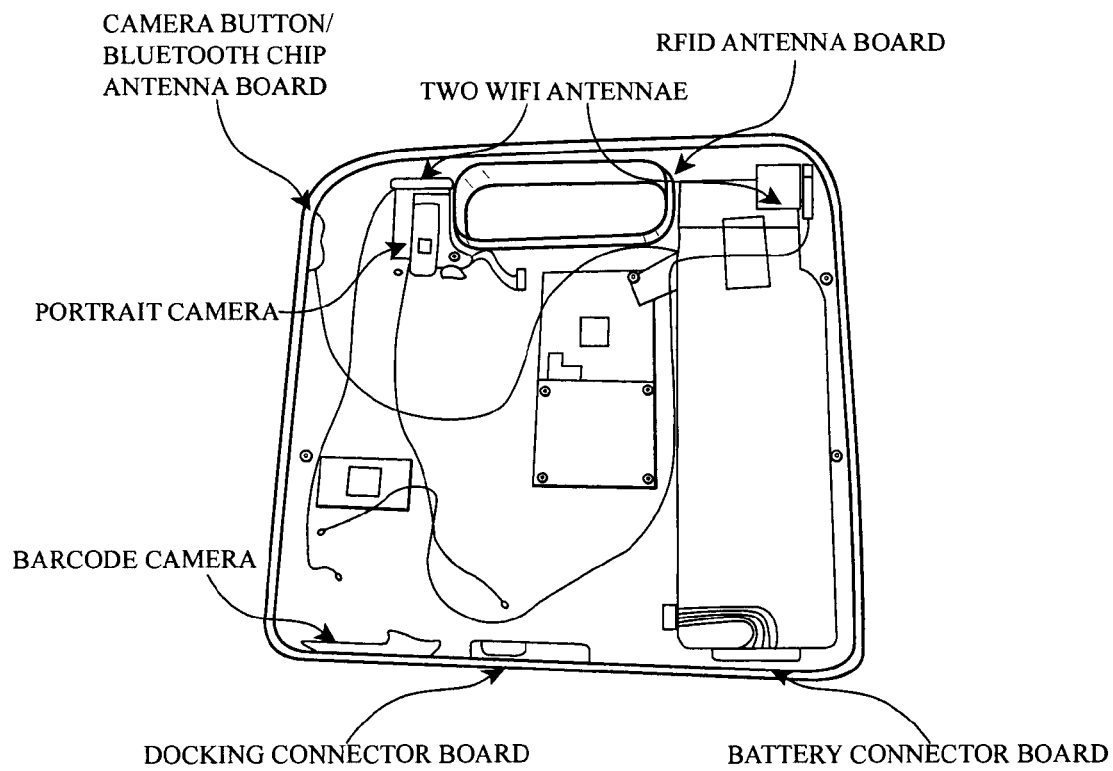
FIG. 5 in a depiction of the inside of the chassis illustrating exemplary placements for antennae according to the present invention.

FIG. 5 illustrates an exemplary placement of a camera button, blue tooth chip antenna board, Wi-Fi antenna, RFID antenna board, battery connector board, docking connector board, barcode camera, and portrait camera in a chassis. Design criteria for component placement may include factors such as magnetic and electrical shielding, thermal shielding or dissipation, RF interference, space constraints, and ergonomics. This list, however, is merely illustrative and not exhaustive of the considerations necessary for component placement; and no single solution may necessarily be better than others.

As previously mentioned, the device will ordinarily include a display screen, such as an LCD, TFT, or other light-weight, portable display. The illustrative system uses an AND Displays 10.4" inch color TFT/LCD Module, model ANDpSi104EA5S-HB. This display supports XGA (1024 (H)×768(V)) screen resolution and 262K (RGB 6-bits data driver) or 16.7M (RGB 8-bits data driver) color depths. The input signals are LVDS interface compatible and it uses a single side-firing CCFL backlight.

Power consumption is 3.7 W typical (using standard SMPTE test pattern) when running at full intensity of 180 nits (cd/m2). Power consumption at 60 nits is 2.87 W. The LCD display, a digitizer, and motherboard may be mated as a single assembly, and shock-mounted to the chassis. The system may also include a backlight inverter (see FIG. 1).

An embodiment of the system includes a DB-15 connector for VGA external display connection, but will ordinarily be unused, as VGA connectors are not sealable. The connector is typically not stuffed on motherboards that are assembled into a chassis, but users requiring external video may desire a tablet PC that offers this feature.

The system may also incorporate a digitizer (see FIG. 1). In the illustrative embodiment, the digitizer is a Wacom SU-001-A 10.4" diagonal electromagnetic (inductive) digitizer that underlaps the LCD. This digitizer has a true resolution accuracy of 0.001 mm (2540 dots/inch) and may report up to 133 points/second during stylus motion.

Figure 6:
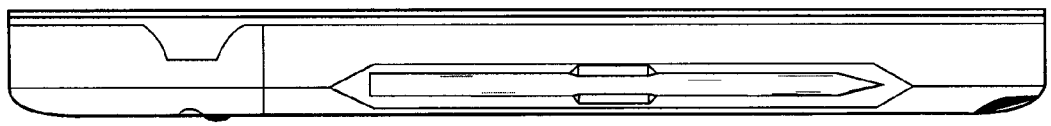
FIG. 6 illustrates an embodiment of the present invention incorporating a stylus and recessed caddy within the chassis of a tablet-style PC.

The system may also be equipped with a stylus, to permit data entry directly into the device via the digitizer. In the illustrative embodiment, the stylus is passive. A suitable stylus device includes the Wacom "Penabled Tablet PC Slim Pen", model MP200-00 that is 5.5 mm in diameter. The pen can report 256 different levels of pressure when the stylus is pressed against the acrylic LCD protector. The stylus can be sensed at distances between 5 mm and 14 mm away from the digitizer board (this includes the thickness of the LCD panel, air gap, and a protective acrylic cover). The system may accommodate the stylus in a recessed caddy area, as shown in FIG. 6.

Tablet PC also refers to a computer, such as a personal computer or a mobile computing device, incorporating various convenient and intuitive aspects of pencil and paper into a user's interaction with the computer. The term "computer" may include at least one central processing unit or CPU (processor) connected to a host bus. The CPU may be any of various types, including an x86 processor, e.g., a Pentium class, a PowerPC processor, a CPU from the SPARC family of RISC processors, as well as others. The computer system may also include various memory mediums, typically including RAM and referred to as main memory. The main memory may store one or more programs implementing the present invention. The main memory may also store operating system software, as well as other software for operation of the computer system. The term "mobile computing device," as used herein, means any computing device intended to move location while maintaining functionality. Mobile computing devices can include, for example, laptop computers, sub-notebooks, personal digital assistants, portable data terminals, tablet PCs, and even smartphones.

To facilitate data and software storage, the system may contain at least one mass storage device, such as an integrated hard disk drive (HDD). Illustratively, the HDD may be a Toshiba 20 Gigabyte 1.8-inch diameter drive, model MK2008GAL. This HDD uses PATA as the interface to the baseboard. There is typically provided a PATA connector directly on the on the baseboard that may be used for a ribbon-cable connection to the "CE" style connector on the HDD. This drive is 5.0 mm thick, making it suitable for use in a portable device such as a tablet PC.

The illustrative embodiment of the tablet PC may include a wireless LAN subsystem. This may consist of a MiniPCI connector on the motherboard, with a Wi-Fi card installed. The commercially available Intel PRO/Wireless 2915 ABG is suitable for use in the illustrative embodiment. It supports the IEEE industry standards 802.11a, b and g.

Certain peripheral devices may be connected to the tablet PC via wireless LAN or Bluetooth technology. The present device may, therefore, also incorporate a Bluetooth controller such as the Taiyo Yuden EYSFCCSXX module, to provide Bluetooth capability for the system. This device incorporates the CSR (Cambridge Silicon Radio) "Bluecore 4" radio chip, operating in the 2.4 GHz band. The module implements Bluetooth 2.0 specifications, and includes AFH (advanced frequency hopping) and EDR (enhanced data rate) functions. The module interfaces to the system using one of the USB ports available via the ICH.

The Taiyo Yuden EYSFCCSXX module also supports WiFi coexistence "Phase 2" capability. This reduces the interference between the Bluetooth and the WiFi radios when they are operating simultaneously. The two modules have a communication channel that they use to inform one another about when they are transmitting, and what WiFi channel is being used. The Bluetooth module attempts to choose a different channel in the 2.4 GHz band which does not conflict with the WiFi channel in use (determined by access point association).

The WMTS subsystem may also include a "dual stuffing option" connector layout on the motherboard. The motherboard, therefore, may contain contacts ("pads") for both MiniPCI and MiniCard (aka Mini-PCI Express) socket connectors. These pads are designed to use substantially the same physical volume inside the system.

An OEM employing this feature would determine, at manufacturing time, which connector to solder to the motherboard, since most compact chassis layouts will permit only one can be used at a time. Then the OEM may insert the appropriate form-factor WMTS card into the system before sealing the chassis.

In instances where the tablet PC user will benefit from having an RFID reader incorporated into the device, a suitable hardware solution may include the Texas Instruments 7961 RFID reader chip and companion MSP430 microcontroller. This device may be connected via an RS-232 interface at TTL levels (i.e., +5 VDC and Ground, vs. the more conventional +12 VDC and −12 VDC) to the COM2 port of the Super-IO. This T.I. chip supports RFID protocols ISO 15693, ISO 14443, and T.I.'s "Tag-It".

The RFID reader is a relatively low power device and has a short reading range on the order of 4 to 5 centimeters. Its antenna should be positioned as far away from any metal as reasonably possible, to read effectively. As a result, the user should position the RFID-tagged object near the antenna location for scanning.

An audio subsystem may be incorporated into the device to provide sound output. One suitable device is based on a Realtek ALC202 codec, which is compliant with the AC'97 specifications. The system may also contain an internal power amplifier to more effectively drive the internal speaker. Exemplary of such amplifiers is the LM4960SQ. A single mono speaker, a custom-designed piezo-electric transducer, can provide rudimentary audio output. The transducer may be mounted to the back of the display screen protector in the area between the medical peripheral slot (stethoscope) and the handle cutout. If higher-quality audio output is desired, a Bluetooth headset may be used, to avoid the need to add I/O ports to the chassis. For that same reason, the illustrative embodiment employs a microphone input via a Bluetooth headset when sound is desired.

In order to avoid increased risk of penetration by fluids and contaminants, the tablet PC will generally not include externally accessible audio I/O jacks, as such jacks would create difficulties in maintaining the sealed nature of the system. If for any reason the end user requires external audio jacking, a USB audio device (e.g., Creative SoundBlaster Audigy 2 NX) may be installed into one of the free USB ports in the dock.

Figure 7:
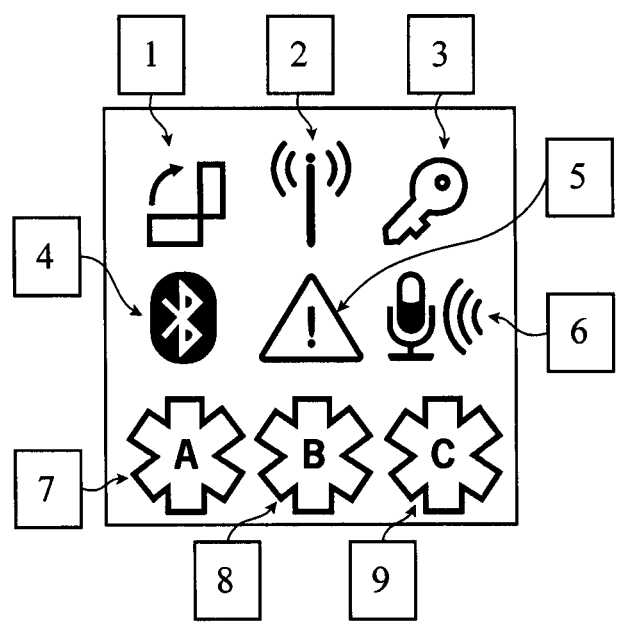
FIG. 7 illustrates an embodiment of cognitive aids.
Figure 8:
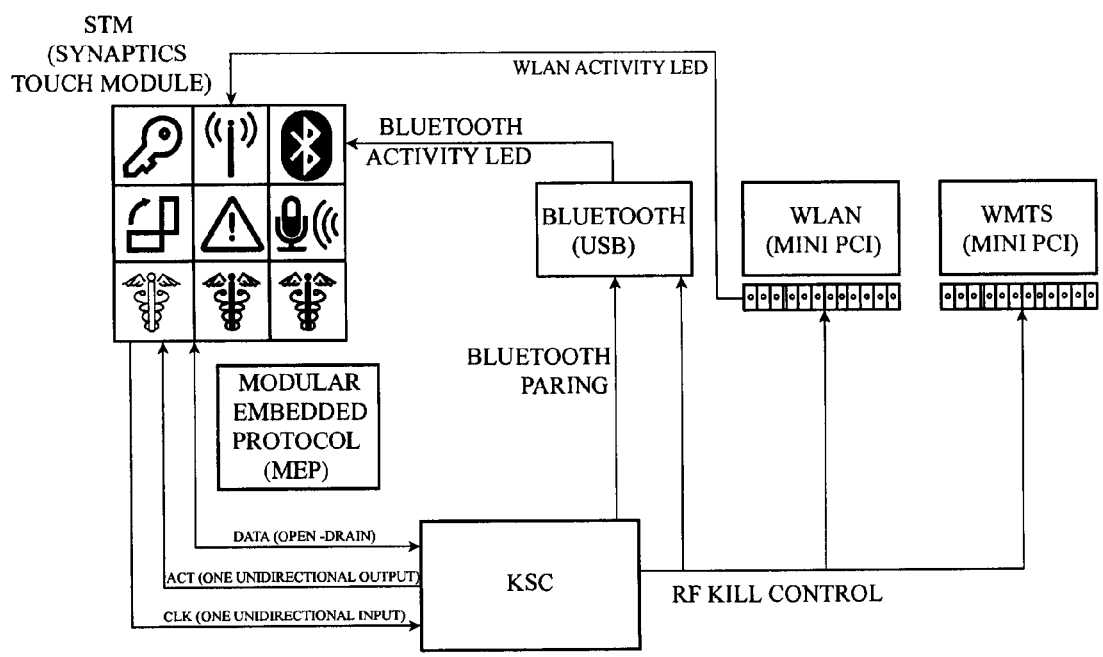
FIG. 8 illustrates cognitive aids and a block flow diagram of a possible architecture for use of the cognitive aids in connection with the hardware of the present invention.
Figure 9:
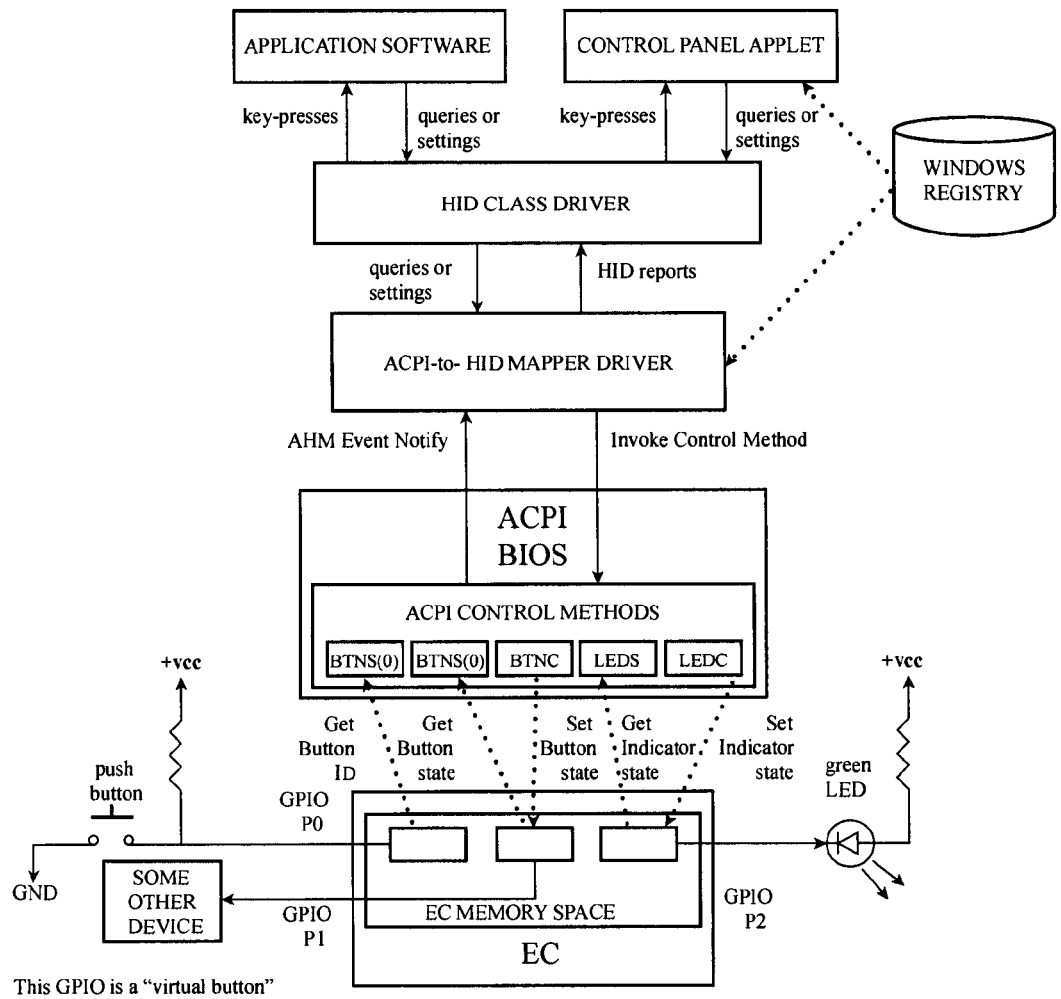
FIG. 9 illustrates an embodiment of an ACPI-to-HID mapper driver architecture.

The system integrates a number of buttons and indicators, the functions and features of which are illustrated in FIGS. 7-9. Each button is assigned a "button number" which refers to the button ID assigned by the KSC. This number may be used by the KSC to report button presses to an ACPI-to-HID mapper driver. HID refers to Human Interface Device. This driver may then translate the button press into an HID code for further processing. The system may include "soft" buttons. A "soft" button is one managed by the Synaptics mobile touch module (STM); there is no tactile feedback from these capacitive buttons. A "hard" button is a physical momentary switch that includes tactile feedback. A "virtual" button does not have a user-accessible physical existence; it is only a software-controllable abstraction of a GPIO signal that can be driven by the KSC.

HID class buttons are buttons reported in the form of HID input messages, as described in specifications promulgated by the USB Implementer's Forum, for example: USB Serial Bus Specification, Revision 2.0, 27 Apr. 2000; USB Device Class Definition for Human Interface Devices (HID), version 1.11, 27 Jun. 2001; USB HID Usage Tables, version 1.12, 21 Jan. 2005.

The "STM" refers to the Synaptics mobile touch module, a commercially available product which may be used in accordance with the illustrative embodiment of the invention. Other button-handling solutions will be recognized by those skilled in the art and are contemplated by the present invention. The STM may contain both capacitive buttons and LEDs integrated into a single package. The STM interfaces to the KSC using a "MEP" protocol defined by the manufacturer.

The illustrative device will generally include a power button that is used to turn the system on and off, and also to put a running system into sleep or hibernate modes (per Windows Control Panel configuration settings, when a Windows O/S is used). The KSC monitors the user press of a physical button and sends onward the appropriate signal to the power and voltage regulation circuitry. In addition, the KSC monitors the CPU state as represented by status pins on the ICH, and may reflect the appropriate status condition on a power LED.

The applet may respond to the HID code by instructing the KSC to power-up the camera and RFID readers, turn on the white illumination LED, and then via USB instruct the camera to grab image frames for barcode analysis and decoding. Simultaneously, via an RS-232 interface, the RFID reader may be instructed to begin searching for nearby RFID tags. When either one of the barcode decode or RFID scanning functions returns a successful result, the applet may instruct the KSC to turn off the illumination LED, power-down the camera, and the RFID reader. As used herein, "applet" generally refers to a software component that runs in the context of another program, such as a web browser or another defined framework. An applet usually performs a narrow function that has no independent use.

Synaptics Touch Module (STM) soft buttons may be used for various system management functions. The STM can contain an embedded microcontroller that interfaces to the KSC using a "MEP" (Modular Embedded Protocol) interface. When the STM reports a button press to the KSC, the KSC sends an SCI interrupt signal to the ACPI framework. This is delivered to the ACPI-to-HID mapper driver which translates it into the appropriate HID button code. An applet responds to the HID code by performing the appropriate function, and in some cases, instructing the KSC to turn on or off specific LEDs by forwarding the command to the STM. In one embodiment of the invention, wireless activity status LEDs (for either or both WiFi and Bluetooth) are driven to the STM directly by the wireless card(s) rather than via the KSC. A performance advantage may be gained in this manner.

For security, a device such as the Infineon SLB9635TT TPM may be used to store credentials securely on the computing device. This device is packaged in a 28-pin TSSOP package, and connects to the ICH via the Low Pin Count (LPC) bus. It is compliant with TPM 1.2 specifications.

Figure 10:
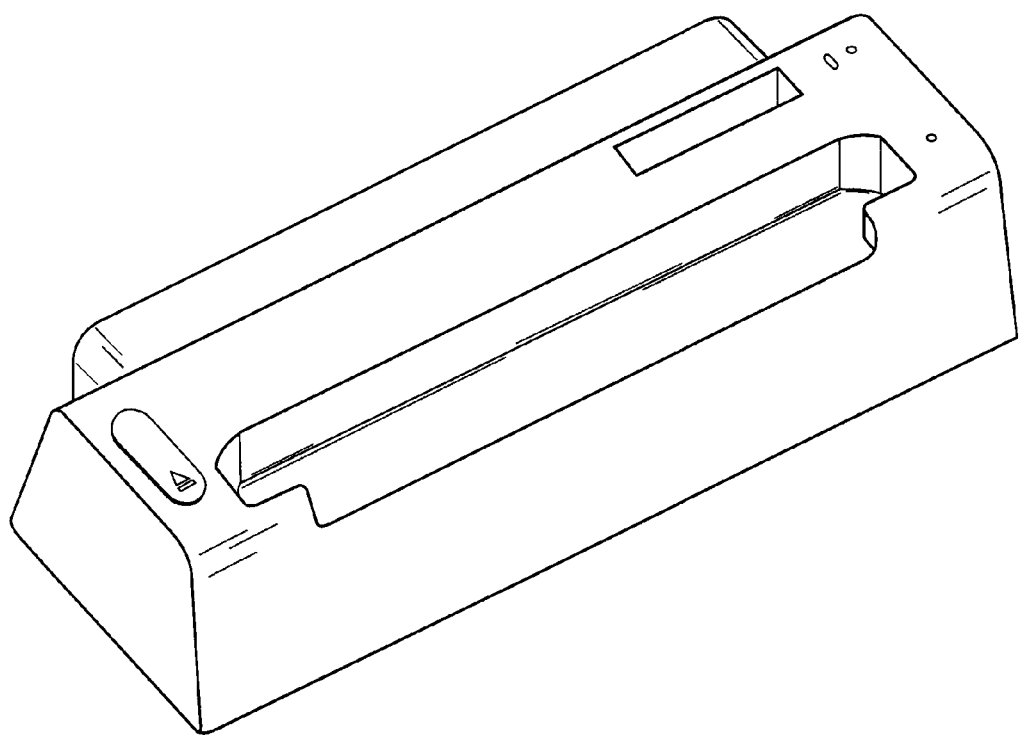
FIG. 10 is a perspective view of an embodiment of a docking station according to the present invention.
Figure 11:
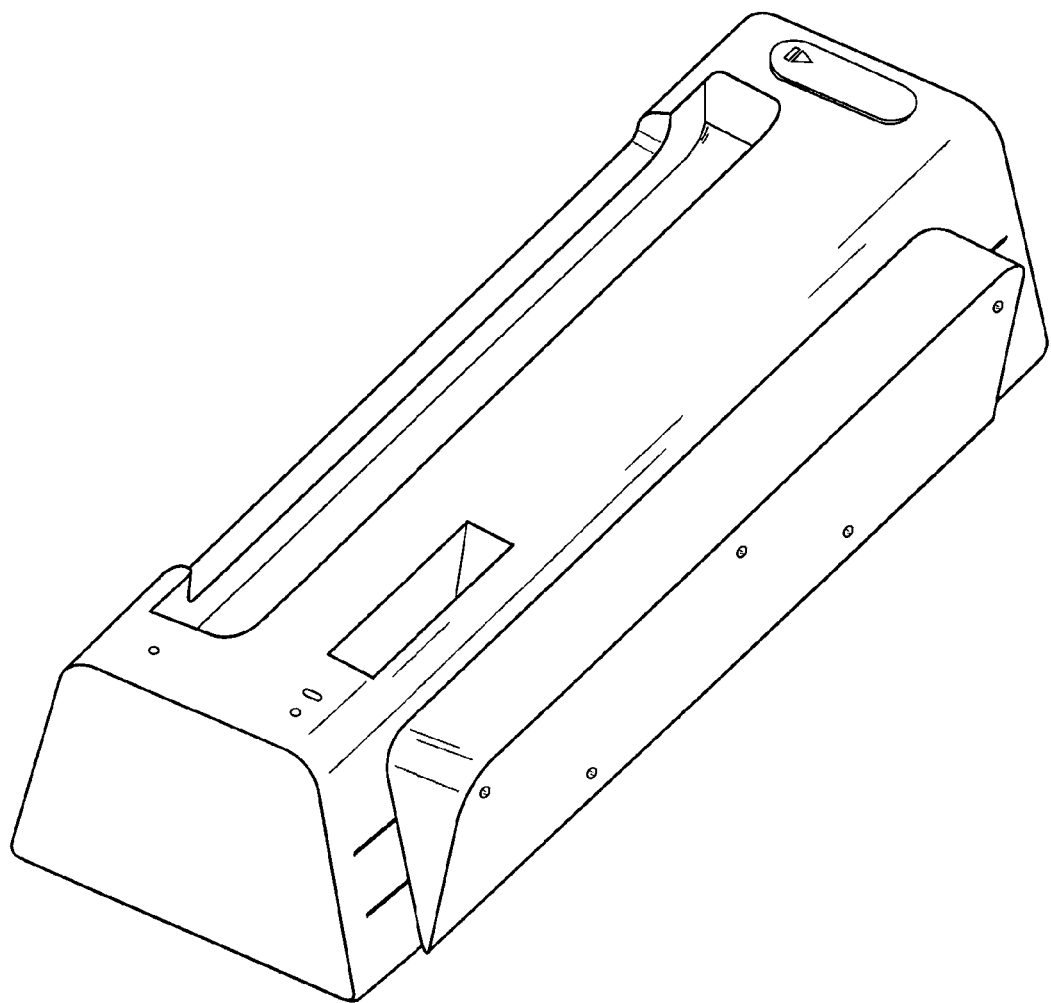
FIG. 11 is another perspective view of an embodiment of a docking station according to the present invention.
Figure 12:
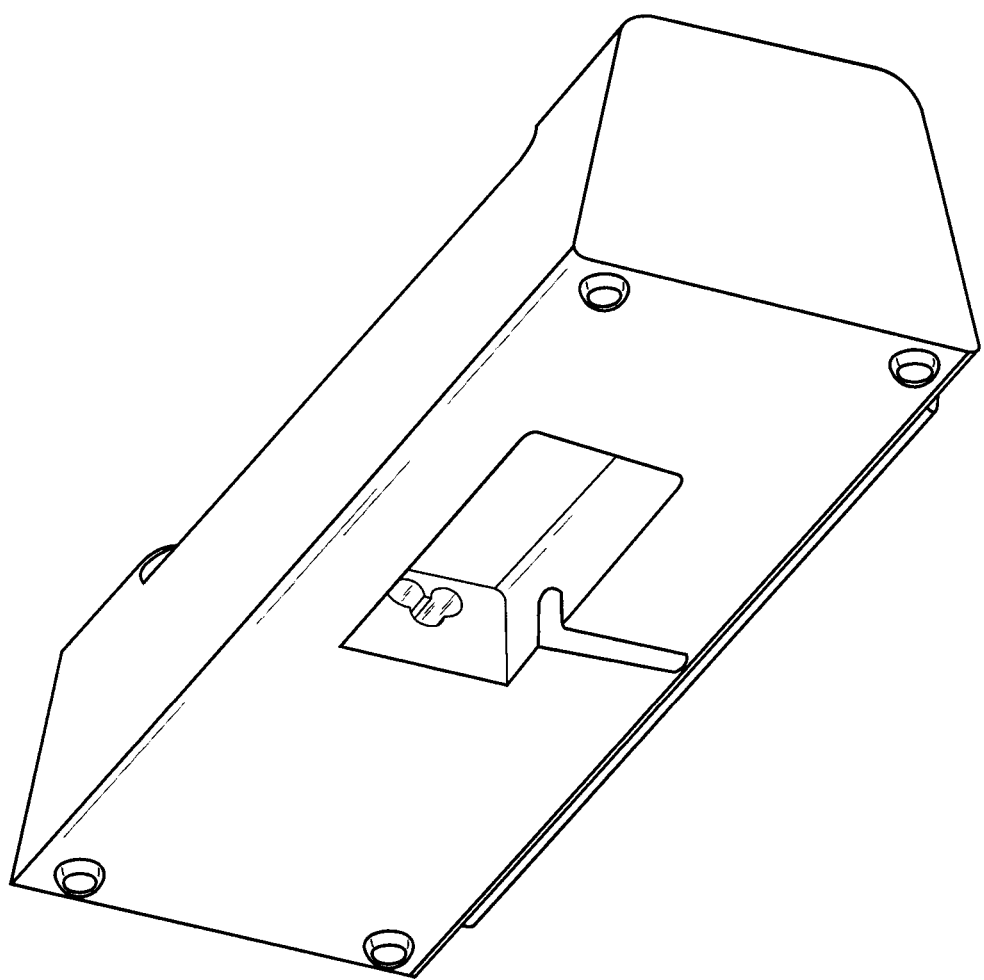
FIG. 12 is a perspective view of an embodiment of a docking station according to the present invention showing the bottom of a docking station.

The tablet PC user may desire a "dock" for the tablet PC. The device may be inserted into the dock to recharge the batteries and to add additional functionality to the device via additional I/O ports, external graphics ports, etc. An embodiment of the dock is illustrated in FIGS. 10-12. The dock is preferably configured to house the tablet PC in a manner that allows it to stand upright and still have the screen be completely viewable. It might include battery charging contacts for the tablet, as well as a charging cavity for a spare battery. LED indicators can be provided to communicate charging status.

The dock may contain a USB hub (presently, USB 2.0 is the most common solution). USB functionality may be implemented with a device such as the Philips ISP1520 USB controller chip in an LQFP64 package. The hub chip has 1 upstream port (goes to the docking connector) and 4 downstream ports. Of the 4 downstream ports, 3 of them are exposed as external USB "type B" sockets. The final downstream port connects to the Ethernet chip. The hub supports USB2.0 data transfer at high-speed (480 Mb/s) and at legacy (USB1.1) full-speed (12 Mb/s) and low-speed (1.5 Mb/s) rates.

The dock may also contain an Ethernet (IEEE 802.3) interface. This might be implemented with the Asix AX88772LF chip in a LQFP128 package The Ethernet chip, desirably, contains both MAC and PHY in a single package, and supports USB2.0 and 802.3 operation at 100 Mb/s and 10 Mb/s. The Ethernet interface may be available on the dock via an external RJ45 socket. A docking connector, in the figures shown as a flush-mounted, injection molded port, provides power and USB connectivity between the tablet PC and the dock. The dock will, generally, also include necessary A/C power components and cabling.

Figure 13:
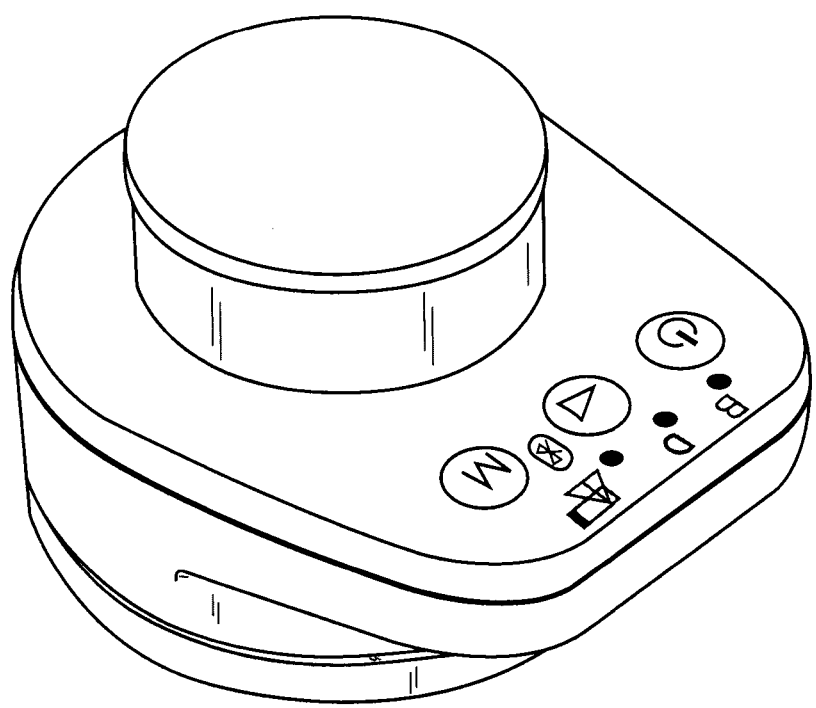
FIG. 13 is a perspective view of an embodiment of a wireless stethoscope.

An illustrative embodiment of the tablet PC includes at least one peripheral data-acquisition device for use by healthcare professionals. Such a device might include a Bluetooth-enabled stethoscope, as shown in FIG. 13, for use by a clinician to examine heart and lung sounds of patients. The stethoscope may include a rechargeable battery (or non-rechargeable battery) and be capable of transmitting audio-output directly to a headset worn by the user (typically the headset will also be Bluetooth-enabled). Alternatively, the stethoscope may transmit to the tablet PC and the tablet PC retransmit the audio output to a headset worn by the user or play the sound via the tablet's internal audio system and speaker.

The stethoscope may include numerous buttons and indicators to permit the user to change the audio output device, set the type of measurement being taken, and perform basic functions (such as turn the device on and off). The stethoscope may also transmit information to the tablet PC relating to battery level, include audio filters to permit more accurate audio representation of a patient's heartbeat, lung function, etc., or include other functions desired by the healthcare professional.

Those skilled in the art will readily recognize how to implement low-level software features such as the system BIOS. In the illustrative tablet PC, however, the BIOS may be configured to implement ACPI control methods for abstracted application control of buttons and LEDs that are managed by the KSC. Applications generally send HID messages, which are processed by the ACPI-to-HID mapper driver, which in turn invokes the ACPI methods in the BIOS. When a button is pressed, the BIOS generates a "notify event" to the operating system. The driver will capture this event, and call the BTNS method to obtain the details of the button press event.

Further, the ACPI-to-HID mapper driver may provide a system-independent way for application software to control and communicate with buttons and LEDs integrated into a computing device that are controlled by the Keyboard/System Controller (KSC). This driver may simultaneously exist as an HID class mini-driver (for interfacing to the Windows operating system and applications) and an ACPI Driver (for interfacing to the BIOS and the KSC).

On its top interface, the ACPI-to-HID mapper driver communicates with the HID class driver to obtain HID LED setting messages ("output reports"), and to deliver HID button input messages ("input reports"). The driver automatically configures itself by reading configuration information from a registry, such as a Windows registry (in instances where a Windows operating system is used, as in the illustrative embodiment which might use the Windows XP Tablet Edition 2005 operating system) in order to know the HID codes that it should pay attention to (for LED settings) and the HID codes that it should generate (for button presses).

On its bottom interface, the driver registers for ACPI Events generated from the BIOS plus KSC, and invokes ACPI Control Methods to send commands to the BIOS plus KSC. The KSC (also known as the EC) actually connects to buttons and LEDs integrated into the system.

The BIOS may also implement ACPI control methods for reporting the temperature values of thermal sensors that are managed by the KSC or for reporting the power usage values of wattage sensors.

Figure 14:
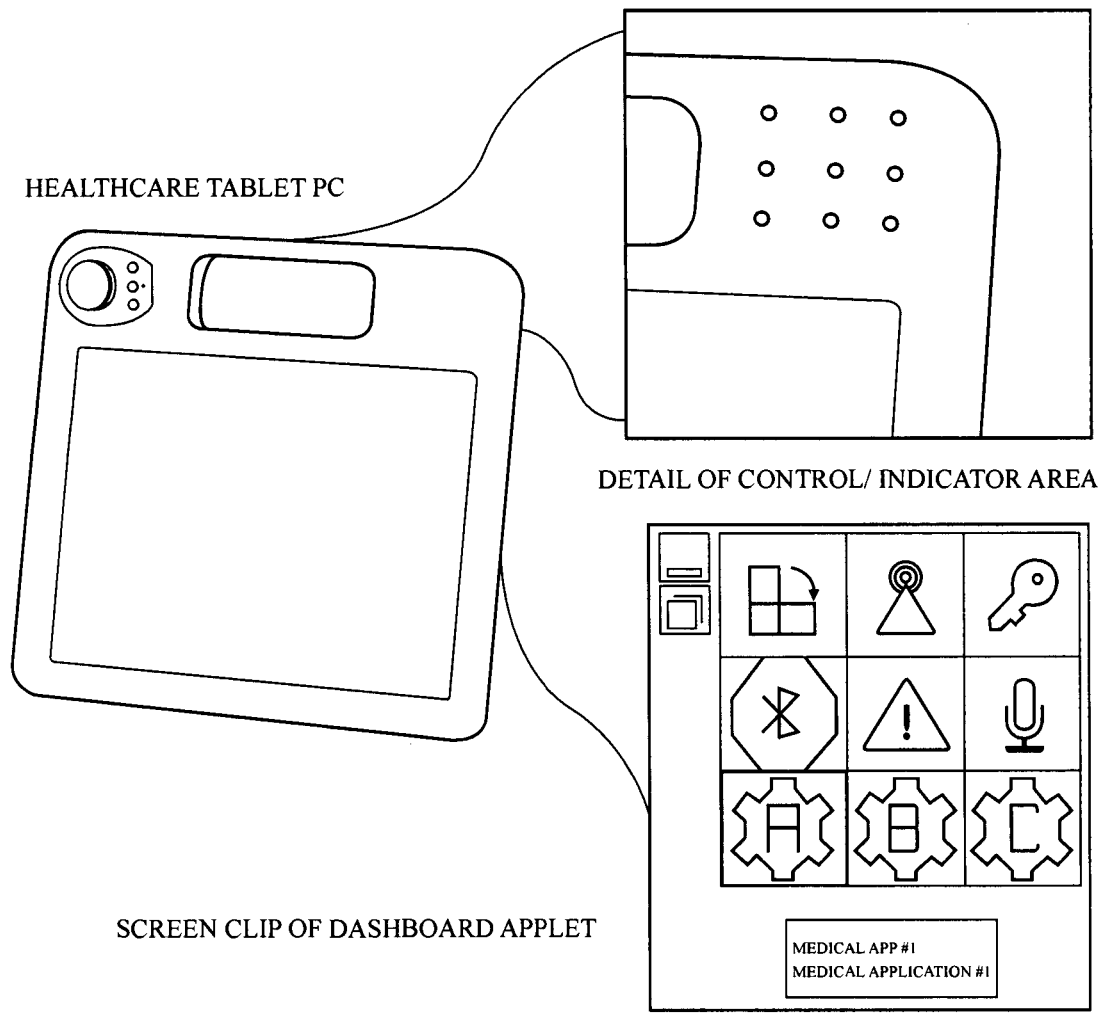
FIG. 14 illustrates an exemplary embodiment of a control/indicator area and applet.

In accordance with an embodiment of the invention, the illustrative tablet PC includes buttons providing various system functions while still maintaining its fluid-resistant sealed design. The buttons facilitate user input. The buttons may be, for example, touch-sensitive. In addition to the buttons array, buttons and a GUI of a "dashboard applet" is provided, as illustrated in FIG. 14. The dashboard applet may be, for example, a Systray applet that controls the operation of the device by detecting button presses, performing the associated actions, and changing the state of LEDs associated with the buttons as appropriate. The dashboard applet provides end-user assistance in the form of on-screen "tool tips" whose visibility can be exposed or hidden.

The applet becomes aware of any HID-class buttons and LEDs because it interfaces with the HID class driver (see FIG. 9). The HID class driver centralizes all HID class activity on the computer, regardless of the originating driver (e.g., ACPI-to-HID mapper driver, USB keyboard driver, Bluetooth keyboard driver) for the activity. The applet then becomes aware of (e.g., by reading the system registry) the correct HID message formats and content necessary to communicate with all of the HID-class buttons. The system registry would therefore contain all of the necessary HID message formats.

In an embodiment of the invention, the buttons include a touch-sensitive button array. The array may be located, for example, to the right of the chassis handle, as shown in FIG. 14. Alternatively, the array can be located along a bottom portion of the chassis (not shown). The button array may further include an LED array that illuminates the buttons in accordance with the desired functionality of the buttons as described in more detail below. A user can manipulate the buttons from an exterior surface of the mobile computing device. As an alternative to buttons, the present invention contemplates employing other suitable input vehicles such as switches, touch-sensitive transducers, dials, knobs, sliders, etc. As an alternative to LEDs, the present invention contemplates utilizing liquid crystal displays and vacuum fluorescent displays. FIG. 14 illustrates an embodiment with nine buttons having LED indicators, although any suitable number of buttons and indicators may be employed. Not every button must have an associated LED. Indeed, the present invention contemplates a device without LEDs.

In an embodiment of the invention, the function of one or more of the buttons and LEDs can be tailored to the usage model of the vertical market segment. The device can therefore be optimized for the usage needs of end users such as medical practitioners in a hospital or clinical setting, although one skilled in the art will appreciate that many variations may be practiced.

In an embodiment of the invention, a printed circuit board for the button array is internally mounted and connected to the mobile computing device via an electrical "bus" interface. The illustrated embodiment employs a GPIO interface via the embedded controller (or the KSC) that emulates the interface for the bus of the printed circuit board. The embedded controller has the firmware for emulation, and presents information from the printed circuit board and translates it to be ACPI compliant before being sent to the BIOS. Operating system has access to subroutines in the BIOS via an ACPI class driver. One skilled in the art will appreciate that various buses may be employed, including but not limited to USB, FireWire, PS/2, PCI, and PCI Express. This electrical "bus" interface allows three classes of operation between the software (such as, for example, device drivers and/or application programs) and the hardware to: (1) receive events when the physical buttons are pressed by the user; (2) query/determine the current state of the LED indicators; (3) turn on or off the LED indicators, accordingly; (4) query/determine a current state of the GPIOs; and (5) turn on or off GPIO signals (also called "virtual buttons"). The GPIOs may be used for various internal functions, including for example enabling/disabling radios, power management, and managing internal hardware devices such as cameras, barcode readers, wireless communications controllers, docking connectors, etc.

According to an embodiment of the invention, dashboard applet cognitive aids are associated with the user input vehicles (e.g., the buttons and indicators) and preferable are tailored for the intended use of the tablet PC. The cognitive aids provide relative information to the user regarding the associated input vehicle. In an exemplary embodiment as shown in FIG. 7, the following can be employed:

1. Visual representation of the cognitive aids can be presented in a full/expanded mode, hidden, or reduced. In a preferred embodiment, the on-screen graphics appear in a semi-transparent manner, to avoid obscuring the underlying screen graphics. In a particularly preferred embodiment, the on-screen graphics transition to a more opaque look when the mouse cursor hovers over them.
2. Each on-screen button representation can change its appearance (e.g., color) to highlight the state of the associated indicator LED or GPIO. For example, when the patient alert LED is illuminated, the on-screen graphic can change from a white background to a yellow background.
3. Each on-screen button representation can be associated with a textual hint or "tool tip" that appears when the mouse cursor hovers over the on-screen graphic. This tool tip can be presented in language appropriate for the user.
4. Each on-screen button representation can additionally be associated with an audible hint or "voice prompt" that is heard when the user presses the physical button. This voice prompt can be presented in any language appropriate for the user. Differentiated voice prompts can be played depending on the current state of the GPIO or associated LED indicator. For example, the first time the voice annotation button is pressed, the LED can be illuminated and the voice prompt can play "recording started." A subsequent press can cause the LED to be turned off and the voice prompt can play "recording finished."

In a preferred embodiment of the present invention, the requirements of the dashboard applet include one or more of the following:

1. Detecting button presses, performing associated functions, and changing the state of associated LEDs as appropriate.
2. Providing clear explanations of the functionality of buttons, preferably through a combination of on-screen tips and voice messages.
3. Providing instructions for recovering from accidental or incorrect button presses and restoring the computer to its previous state. The Synaptics Touch Module (STM), noted above, provides the ability to reject false button presses to a certain extent.
4. Providing a method for assigning configurable buttons of the touch-sensitive button array (see FIG. 14), and preferably also allowing system designers to create registry entries that is published accordingly so that applications can be written to push down settings for the configurable buttons, for example via the system registry. In an exemplary embodiment of the invention, three buttons can be configurable for site-specific applications such as: (1) in-patient electronic medical records; (2) out-patient electronic medical records; and (3) physician medical information reference.
5. Providing a method for switching a "locale" setting for the computer, and adapting the text and voice prompts accordingly for the selected locale. For example, some sites may have a user population fluent in more than one language, such as English and Spanish in the U.S., and English and French in Canada.
6. Thermal sensor temperature reporting, and other advanced computer monitoring and maintenance functions.

According to an embodiment of the invention, the dashboard applet runs automatically when the user logs in. The touch-sensitive button array and dashboard applet may additionally be responsible or provide assistance for camera capture, barcode or RFID scanning, wireless device pairing, wireless network connection, radio operation, audio settings, handwriting recognition, and user authentication.

In the embodiment of FIGS. 7 and 14, having nine buttons with LED indicators, the buttons may have functionality as set forth in the following table.

| | | | |
|---|---|---|---|
| Button 1 | Screen image rotation, 90 degrees per press. | | (No accompanying LED indicator) |
| Button 2 | Wireless radio activation and deactivation, toggles between the two settings. | LED 1 | Wireless radio activity; indicator flashes green according to activity level. |
| | | LED 2 | All wireless radios deactivated; indicator shows yellow when deactivated. |
| Button 3 | Computer security action sequence, equivalent to "Control Alt Delete". | LED 3 | Computer is secure when indicator shows yellow. |
| Button 4 | Initiate wireless communication pairing sequence. | LED 4 | Wireless communication radio activity; indicator flashes blue according to activity level. |
| Button 5 | Patient alert. | LED 5 | Indicator flashes red when patient needs attention. |
| Button 6 | Start/stop recording voice annotation, toggles between the two settings. | LED 6 | Actively recording audio when indicator shows red. |
| Button 7 | Activate medical application 1. | LED 7 | Green status indicator as programmed by medical application 1. |
| Button 8 | Activate medical application 2. | LED 8 | Green status indicator as programmed by medical application 2. |
| Button 9 | Activate medical application 3. | LED 9 | Green status indicator as programmed by medical application 3. |

In an embodiment of the invention, the appearance of the cognitive aids (i.e., the on-screen tips) consists of two components: (1) the application shows an icon in the system tray and allows the user to bring up associated menus for visibility of on-screen tips (e.g., hidden, visible, and expended), locale selection (e.g., English, Spanish, French), about (e.g., copyright and version information), and exit (to exit the dashboard applet); and (2) on-screen tips provide a GUI including an explanation of the touch-sensitive button array, and can appear in hidden, visible, and expanded views that take up different amounts of space on the screen. The tips preferably have an "always on top" default setting and can additionally be 50% transparent so that the underlying screen can still be seen. Additionally, the tips may change to 0% transparent when the cursor moves over them. In the hidden view, there are no tips on the screen. In the visible view, for example, a limited number of tips can be displayed. In an embodiment of the invention, the tips are limited to the three configurable medical applications. In the expanded view, for example, the tips for all of the touch-sensitive buttons can be displayed. It is to be understood that a wide variety of appearance attributes of the dashboard applet are contemplated by the present invention.

In an embodiment of the invention, the appearance and other characteristics of the on-screen tips are configured from the system registry.

An embodiment of the present invention includes a general purpose method for loading program subroutines, such as an ACPI-to-HID mapper driver, into an operating system such as Microsoft Windows, Linux, etc., for invoking ACPI control methods via the operating system and/or application software running in the context of the operating system. The ACPI-to-HID mapper driver allows manipulation of hardware in an operating system and allows the behavior resulting from user input to be hardware-independent. The ACPI-to-HID mapper driver configures itself via an external configuration file that provides system design specifics (e.g., how many buttons and indicators, and their characteristics) and allows a single driver to be used, or re-used, on multiple system designs with minimal or no change.

According to an embodiment of the invention, the dashboard applet provides some behaviors to meet the needs of the system design based on the intended use of the tablet PC, and also provides some end-user cognitive aids for using the hardware. End-user cognitive aids, as used herein, include any type of helpful information communicated to a user of the device. Behavior, as used herein, refers to what does or should occur when the user takes an action with respect to the mobile computing device, such as pressing a button.

Dashboard applet behavior for the buttons and indicators is tailored as appropriate for the intended use of the tablet PC. In an exemplary embodiment of the invention, the device includes wireless communication radios such as Wi-Fi and Bluetooth, each having its own activity LED, an "RF Kill" button, and internal GPIO signals that control the "RF Kill" signal to the radios. In this exemplary embodiment, the dashboard applet incorporates a software algorithm that will: (1) sense when a user presses the RF Kill button; (2) determine the current state of RF Kill operation (i.e., asserted or not); (3) toggle the state of RF Kill operation to its opposite, as requested; (4) when asserting the RF Kill state, turning on the RF Kill GPIO signal to the wireless communication radio(s) and the RF Kill LED; (5) when de-asserting the RF Kill state, turning off the RF Kill GPIO signal to the wireless communication radio(s) and the RF Kill LED. One skilled in the art will appreciate that a variety of algorithms could be employed in response to a user button press stimulus.

The present invention provides a standardized nomenclature and method for using ACPI control methods for controlling buttons, indicators, and similar devices. A single/standard ACPI device driver controls buttons, indicators, and similar devices, and is re-usable from one mobile computing device implementation to another. A configuration file can be used to define the details of a given mobile computing device button and indicator implementation, and those details can be used to control an ACPI-to-HID mapper driver without changing source code for the ACPI-to-HID mapper driver or the applet. A control panel applet can an provide end-user management GUI that gains knowledge about the specific buttons and indicators on a given mobile computing device by reading the configuration file and communicating via a single ACPI-to-HID mapper driver without changing source code for the ACPI-to-HID mapper driver or the applet. "Gains knowledge," as used herein, refers to reading configuration settings stored in a configuration file (e.g., the system registry).

A consistent naming and implementation scheme allows the system designs to be developed more rapidly. Often the most time-consuming development item is the device driver.

This approach allows the driver to be reused from design to design, with only a configuration file change. BIOS and firmware development can be done faster because the interfaces are known in advance and don't need to be specified from scratch. Most of the focus can be applied to the dashboard applet that is one of the key touch points by the target users, and will return the most value.

Example

The following tables set forth exemplary HID codes, associated LEDs, functions, text captions, optional voice messages, and algorithms for each button in the embodiment illustrated in FIGS. 7 and 14.

Button 1: Screen Image Rotation

| | |
|---|---|
| Button Number | 1 |
| HID Code(s) | Page = 0x0c, Usage = 0x01, Button Usage = 0x37. |
| Associated LEDs | None. |
| Purpose | The screen image rotates by 90 degrees (¼-turn) on each button press. This allows transition from landscape to portrait viewing orientation. |
| Text Caption | ENU: "Screen Rotation. Rotate screen image 90 degrees."<br>ESM: "Rotación de Pantalla. Rote la imagen de pantalla por 90 grados." |
| Voice Messages | Message 1A: ENU: "Rotating screen image by 90 degrees. To return the view to the way it just was, press the button three more times." ESM: "Imagen de pantalla que rota por 90 grados. Para volver la visión a la manera que apenas estaba, que presione el botón tres veces más." |
| Algorithm | Capture HID code<br>Play Message 1A<br>Send IO_Control to graphics driver |

Button 2: Wireless Radio Activation and Deactivation

| | |
|---|---|
| Button Number | 2 |
| HID Code(s) | Page = 0x0C, Usage = 0x01, Button Usage = 0x1AD. |
| Associated LEDs | LED1: WiFi activity signal routed directly from WiFi card, with KSC programmatic enable/suppress.<br>LED2: RF Kill indicator. |
| Purpose | Enable/disable all wireless radios, disable is also called "RF Kill". The KSC microcontroller actually performs the RF Kill action, and reports the HID code. |
| Text Caption | ENU: "Wireless. Activate or deactivate all wireless radios."<br>ESM: "Radios sin hilos. Active o desactive todas las radios sin hilos." |
| Voice Messages | Message 2A: ENU: "Deactivating all wireless radios. This results in disconnection from the wireless network and all wireless peripheral devices. To restore connectivity, press the button again." ESM: "Desactivar todas las radios sin hilos. Esto da lugar a la desconexión de la red sin hilos y de todos los dispositivos periféricos sin hilos. A la conectividad del restore, presiona el botón otra vez."<br>Message 2B: ENU: "Activating all wireless radios. This results in reconnection to the wireless network and all wireless peripheral devices. To disconnect, press the button again." ESM: "Activar todas las radios sin hilos. Esto da lugar a la reconexión a la red sin hilos y a todos los dispositivos periféricos sin hilos. A la desconexión, presiona el botón otra vez." |
| Algorithm | Capture HID code<br>If (previous-status == "activated") then<br>    Play Message 2A<br>    Program LED1 to "disabled"<br>    Program LED2 to "on" (yellow)<br>Else<br>    Play Message 2B<br>    Program LED1 to "enabled"<br>    Program LED2 to "off"<br>Endif |

Button 3: Security Action Sequence

| | |
|---|---|
| Button Number | 3 |
| HID Code(s) | Page = 0x01, Usage = 0x07, Button Usage = 0xE0, 0xE2, 0x4C (three characters «Ctrl+Alt+Del» in one packet). |
| Associated LEDs | LED3: system secure indicator. This LED must be programmed by the system security software (e.g., Softex OmniPass) because the dashboard application is not running when the user is not logged in. |
| Purpose | When system is at login screen, start login procedure (note that the dashboard application is not running until the user logs in, so no tool tips or voice prompts are provided at that time). When system is logged in, shows "Windows Security" dialog box where you can logout, lock screen, enter performance monitor, etc. |
| Text Caption | ENU: "Security. Activate Windows Security."<br>ESM: "Seguridad. Active la seguridad de Windows." |
| Voice Messages | Message 3A: ENU: "System security options menu. Click the Cancel button to cancel this operation." ESM: "Menú de las opciones de la seguridad del sistema. Chasque el botón de la cancelación para cancelar esta operación." |
| Algorithm | Capture HID code<br>Play Message 3A |

Button 4: Wireless Pairing

| | |
|---|---|
| Button Number | 4 |
| HID Code(s) | Page = 0x0C, Usage = 0x01, Button Usage = 0x1BB. |
| Associated LEDs | LED4: Bluetooth activity signal routed directly from a wireless (e.g., Bluetooth) module, with KSC programmatic enable/suppress. |
| Purpose | This button is used to initiate wireless (e.g., Bluetooth) pairing in the event that the auto-pairing algorithm embedded in the Bluetooth module needs to be restarted. The KSC microcontroller sends this signal directly to the Bluetooth module and then reports the HID code. The dashboard application can also launch the Toshiba system tray applet so that the user can either observe, or participate in the pairing process. |
| Text Caption | ENU: "Bluetooth. Pair up Bluetooth peripheral devices."<br>ESM: "Bluetooth. Aparéese encima de los dispositivos periféricos de Bluetooth." |
| Voice Messages | Message 4A: ENU: "Beginning to pair up Bluetooth peripheral devices. Close the Bluetooth Settings dialog box to cancel this operation." ESM: "El comenzar a aparearse de los dispositivos perifericos de Bluetooth. Cierre la caja de dialogo de los ajustes de Bluetooth para cancelar esta operación."<br>Message 4B: ENU: "Bluetooth features are currently inaccessible because all wireless radios are deactivated. Please activate wireless radios first." ESM: "Las características de Bluetooth son actualmente inaccesibles porque se desactivan todas las radios sin hilos. Antes de continuar, active por favor las radios sin hilos." |
| Algorithm | Capture HID code<br>If (RF-Kill active)<br>    Play Message 4B<br>Else<br>    Play Message 4A<br>    Launch Bluetooth system tray applet (e.g., Toshiba, IVT)<br>Endif |

Button 5: Patient Alert

| | |
|---|---|
| Button Number | 5 |
| HID Code(s) | Page = 0x0C, Usage = 0x01, Button Usage = 0x10D. |
| Associated LEDs | LED5: Patient alert indicator. |
| Purpose | This button is used to cancel a patient alert notice. Normally, the notice condition is activated by a medical telemetry application that determines patient attention is required. |
| Text Caption | ENU: "Patient Assistance. Activate or deactivate the patient assistance notice."<br>ESM: "Ayuda Paciente. Active o desactive el aviso paciente de la ayuda." |
| Voice Messages | Message 5A: ENU: "Canceling patient assistance notice. To reactivate, press this button again."<br>ESM: "Cancelar el aviso paciente de la ayuda. Para reactivar, presione este botón otra vez."<br>Message 5B: ENU: "Activating patient assistance notice. To cancel, press this button again."<br>ESM: "Aviso paciente de la ayuda que activa. Para cancelar, presione este botón otra vez." |
| Algorithm | Capture HID code<br>If (previous-status == "activated") then<br>    Play Message 5A<br>    Program LED5 to "off"<br>Else<br>    Play Message 5B<br>    Program LED5 to "on" (red)<br>Endif |

Button 6: Voice Annotation Recording

| | |
|---|---|
| Button Number | 6 |
| HID Code(s) | Page = 0x0C, Usage = 0x01, Button Usage = 0xB2. |
| Associated LEDs | LED6: audio recording indicator. |
| Purpose | This button is used to start and stop recording of an audio voice annotation. Since the system does not contain an integrated microphone, it is presumed that a Bluetooth audio headset will already be paired with the system, and selected as the default Windows audio input device. |
| Text Caption | ENU: "Recording. Start and stop recording of a voice annotation."<br>ESM: "Grabación. Comience y pare la grabación de una anotación de la voz." |
| Voice Messages | Message 6A: ENU: "Recording a voice annotation. Begin speaking after the tone. To stop recording, press this button again. «Beep»." ESM: "Registración de una anotación de la voz. Comience a hablar después del tono. Para parar el registrar, presione este botón otra vez. «señal sonora»."<br>Message 6B: ENU: "Recording finished." ESM: "La grabación acabó." |
| Algorithm | Capture HID code<br>If (previous-status == "activated") then<br>    Play Message 6B<br>    Stop recording audio (this step performed by medical application).<br>    Program LED6 to "off" |

|   |   |
|---|---|
|   | Else |
|   |     Play Message 6A |
|   |     Begin recording audio (this step performed by medical application). |
|   |     Program LED6 to "on" (red) |
|   | Endif |

Button 7: Activate Medical Applications 1 Through 3

| | |
|---|---|
| Button Number | 7, 8, and 9 |
| HID Code(s) | Page = 0x0C, Usage = 0x03, Button Usage = 0x01, 0x02, and 0x03. |
| Associated LEDs | LED7, LED8, and LED9: Medical application indicator. The indicators are turned on or off directly by the medical applications without interference from the dashboard application. |
| Purpose | This button is used to launch a configurable medical application. |
| Text Caption | The text captions for the three medical applications will almost certainly be changed by the ISV/System Integrator to match the titles of the assigned/bundled application programs.<br>ENU: "Medical application #1." ESM: "Aplicación médico número 1."<br>ENU: "Medical application #2." ESM: "Aplicación médico número 2."<br>ENU: "Medical application #3." ESM: "Aplicación médico número 3." |
| Voice Messages | Message 7A: ENU: "Launching medical application number one." ESM: "Por lanzar la aplicación médico que numera uno."<br>Message 8A: ENU: "Launching medical application number two." ESM: "Por lanzar la aplicación médico que numera dos."<br>Message 9A: ENU: "Launching medical application number three." ESM: "Por lanzar la aplicación médico que numera tres."<br>These three voice messages can be re-recorded by the system administrator to match the site-local assignments. |
| Algorithm | Capture HID code<br>If (button == 7) then<br>    Play Message 7A<br>ElseIf (button == 8) then<br>    Play Message 8A<br>ElseIf (button == 9) then<br>    Play Message 9A<br>Endif |

The disclosed invention has numerous, practical embodiments. The various embodiments are to inventions useful for those requiring a portable computing platform that is durable and resistant to penetration by fluids. The device is also resistant to chemical and other cleaning solvents used to minimize the spread of germs and bacterial through contact with portable objects in a hospital, clinical, and/or other environments. While the disclosed embodiments relate generally to a portable computing platform for medical professionals, those skilled in the art will readily recognize the need for a computing platform in accordance with the present invention in a wide variety of fields.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A non-transitory machine-readable medium including instructions, which when executed by a mobile computing device, cause the mobile computing device to:
present an applet for the mobile computing device having a user input vehicle, the user input vehicle comprising an element configured to provide an end-user management graphical user interface, the applet to gain knowledge about the user input vehicle by reading a configuration file and communicating via a device driver, the device driver being reusable by multiple applets with only reconfiguration by the configuration file.

2. The non-transitory machine-readable medium of claim 1, wherein the mobile computing device is configured for a variety of sites having different application requirements, and wherein the user input vehicle is configurable for a site-specific application.

3. The non-transitory machine-readable medium of claim 2, wherein a site of the variety of sites is a medical clinic or hospital, and the site-specific application includes one of in-patient electronic medical records, outpatient electronic medical records, and physician medical information reference.

4. The non-transitory machine-readable medium of claim 1, wherein the device driver automatically configures itself from the configuration file.

5. The non-transitory machine-readable medium of claim 4, wherein the configuration file resides in a system registry.

6. The non-transitory machine-readable medium of claim 5, wherein appearance characteristics of the graphical user interface are configured from the system registry.

7. The non-transitory machine-readable medium of claim 1, wherein the element comprises software code or hardware.

8. The non-transitory machine-readable medium of claim 1, wherein the element is a single element.

* * * * *